(12) United States Patent
Atlagic (10) Patent No.: US 11,541,141 B2
(45) Date of Patent: Jan. 3, 2023

(54) STERILIZATION CASSETTE (71) Applicant: Miradex, Ltd., Hinsdale, IL (US)

(72) Inventor: Zeljko G. Atlagic, Hinsdale, IL (US)

(73) Assignee: Miradex, Ltd., Hinsdale, IL (US)

(*) Notice: Subject to any disclaimer, the term of this patent is extended or adjusted under 35 U.S.C. 154(b) by 160 days.

(21) Appl. No.: 17/211,258

(22) Filed: Mar. 24, 2021

(65) Prior Publication Data
US 2022/0305164 A1   Sep. 29, 2022

(51) Int. Cl.
*A61L 2/26* (2006.01)

(52) U.S. Cl.
CPC ............. *A61L 2/26* (2013.01); *A61L 2202/24* (2013.01)

(58) Field of Classification Search
CPC ................................ A61L 2/26; A61L 2202/24
See application file for complete search history.

(56) References Cited

U.S. PATENT DOCUMENTS 4,541,992 A * 9/1985 Jerge ...................... A61B 50/31
422/310

* cited by examiner

*Primary Examiner* — Lessanework Seifu
(74) *Attorney, Agent, or Firm* — Seyfarth Shaw LLP (57) ABSTRACT

Disclosed is a sterilization cassette with a less cumbersome mechanism for opening and closing the cassette, as compared to prior art cassettes. The cassette includes a slider mechanism that couples the cassette closed with pins and hooks on one side, and that allows pivoting of the two cassette pieces with slots and pins on the other side. The cassette can therefore be open and closed with one hand in a simple and easy manner. The cassette can also include inserts that hold instruments in a staggered, multi-layer manner to increase the efficiency of the cassette as compared to the single-layered inserts of the prior art.

17 Claims, 8 Drawing Sheets

STERILIZATION CASSETTE

TECHNICAL FIELD OF THE INVENTION

The presently disclosed embodiments relate generally to sterilization cassettes. More particularly, the presently disclosed embodiments relate to a sterilization cassette with an improved latching system and flexible inserts.

BACKGROUND OF THE INVENTION

Sterilization cassettes are used by those in the dental and surgical industry to clean and sterilize surgical instruments between patient operations. Once an instrument is used, it can be placed inside a sterilization cassette and placed within a cleaning device that is similar to a dishwasher. The cassette generally has apertures that allow water and other cleaning fluid to enter into the cassette and clean the instruments inside. The cassette also has inserts that softly grip the instruments during the cleaning process to ensure they are adequately spaced from one another. A sterilization cassette can therefore act as an easy to carry, portable container that includes all of the necessary items for operating on a patient.

Figure 7:
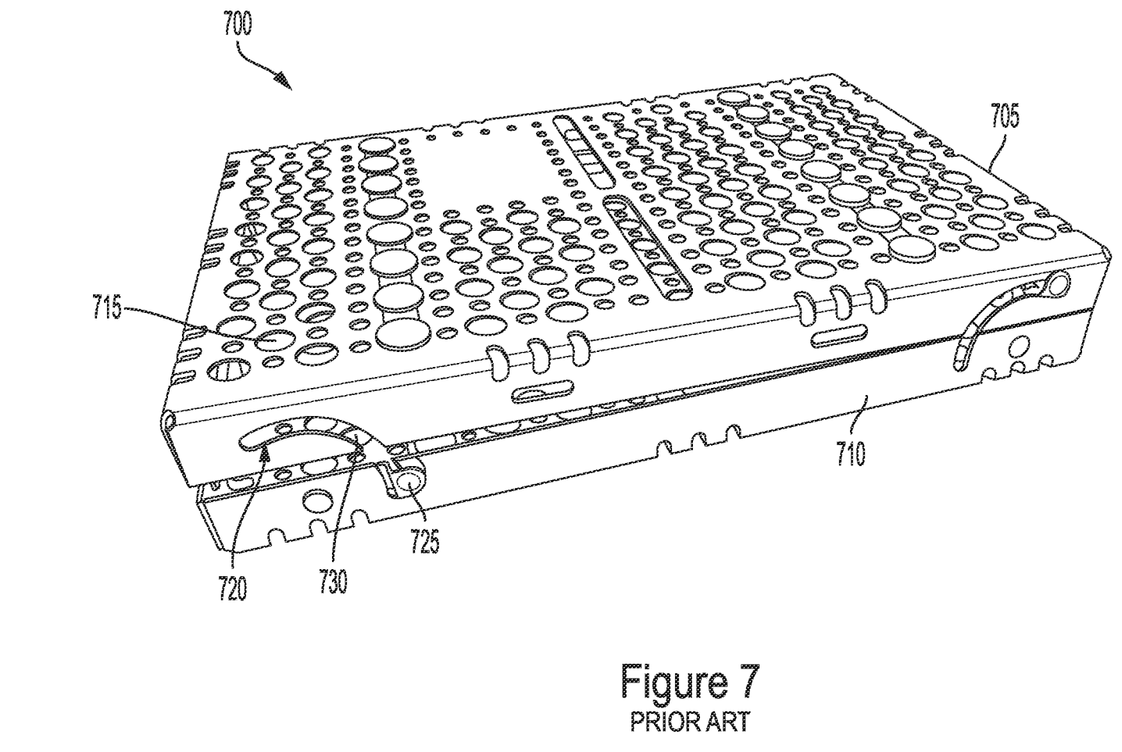
FIG. 7 is a top perspective view of a prior art cassette in the closed position.
Figure 8:
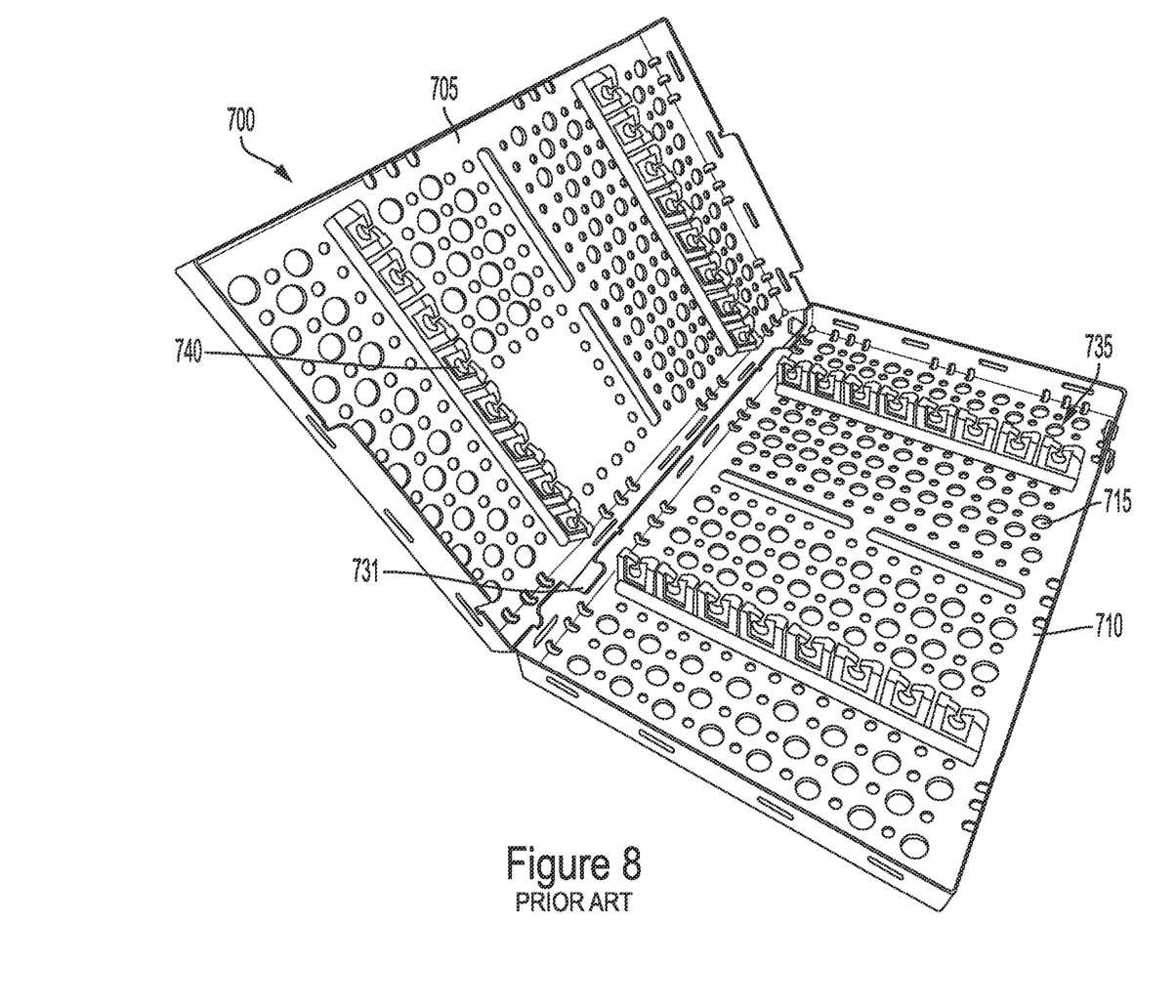
FIG. 8 is a top perspective view of a prior art cassette in the open position.

An exemplary cassette 700 is shown in FIGS. 7 and 8. As shown, the cassette 700 includes a first portion 705 coupled to a second portion 710. Each portion 705, 710 can include apertures 715 for allowing the flow of liquid into the cassette 700 and to clean the instruments inside. The portions 705, 710 are coupled together by a latch system 720 including an arm 725 and a slot 730 that receives the arm 725 inside. As shown in FIG. 8, the first 705 and second 710 portions each include tabs 731 that passively engage one another to allow pivoting of the first 705 and second 710 portions about one another.

FIG. 8 also illustrates the inserts 735 of the prior art cassettes 700. As shown, the insert 735 is a soft, generally rubber or silicone object with indents 740 that receive surgical instruments. A user can therefore place their surgical instruments inside the indents 740 where the instruments will be adequately spaced apart during the cleaning process.

The prior art cassette 700 shown in FIGS. 7 and 8, and prior art cassettes in general, serve their purpose of providing an easy enclosure for holding instruments during cleaning. However, the tabs 731 passively engage one another in a manner that can be difficult to handle on a daily basis. For example, the prior art cassette portions 705, 710 lift away from each other completely when the cassette 700 is opened, and therefore require two hands to open and close. The latch system 720 also requires two hands to operate. Further, the inserts 735 include a basic array of indents 740 for holding instruments, but are not optimally designed for holding the maximum number of instruments within the cassette 700.

SUMMARY OF THE INVENTION

The presently disclosed embodiments relate to a sterilization cassette with an improved closing mechanism and greater ability to hold instruments. The cassette improves upon the cumbersome latch and tab system described above by sliding open and closed with pins and hooks on one side of the cassette, and pivoting with slots and pins on the other side of the cassette. The cassette can therefore be opened and closed with one hand and in a simple manner. The cassette can also include inserts with indents that hold instruments in a staggered, multi-layer manner to increase the number of instruments the cassette can hold while still spacing apart the instruments within the cassette.

In particular, the presently disclosed embodiments comprise a cassette including a first portion, a second portion separable from the first portion, a hook coupled to one of the first or second portions, a coupling pin coupled to the other of the first or second portions and engageable with the hook to couple together the first and second portions at a first end, a pivot pin coupled to one of the first or second portions, and an engagement portion coupled to the other of the first or second portions. The engagement portion is C-shaped and defines a slot therein. The pivot pin is configured to be inserted into the slot to pivotably couple the first portion to the second portion at a second end opposite the first end.

The presently disclosed embodiments also include a cassette including a first portion having apertures, and a second portion also having apertures and separable from the first portion. The second portion is pivotably coupled to the first portion by a pivot system on a first end, and the second portion is removably coupled to the first portion by a coupling system on the second end. The coupling system includes a hook biased into engagement with a coupling pin when the cassette is in a closed position, and the pivot system includes an engagement portion defining a slot that receives a pivot pin to permit pivoting of the first and second portions when the cassette is in an open position. An insert is removably coupleable to at least one of the apertures and including indents configured to hold surgical instruments.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION OF THE EMBODIMENTS

While this invention is susceptible of embodiments in many different forms, there is shown in the drawings, and will herein be described in detail, a preferred embodiment of the invention with the understanding that the present disclosure is to be considered as an exemplification of the principles of the invention and is not intended to limit the broad aspect of the invention to embodiments illustrated. As used herein, the term "present invention" and similar terminology is not intended to limit the scope of the claimed invention and is instead a term used to discuss exemplary embodiments of the invention for explanatory purposes only.

A sterilization cassette is disclosed with a simple and easy mechanism for opening and closing the cassette. The cassette slides open and closed on one side through a coupling mechanism that includes coupling pins and hooks, and pivots in a controlled manner on the other side with pivot pins and slots. The cassette can also include inserts that hold instruments in a staggered, multi-layer manner to increase the efficiency of the cassette as compared to the single-layered inserts of the prior art. The cassette of the presently disclosed embodiments can therefore be opened with one hand and in a simple and easy manner, while efficiently storing a larger quantity of surgical instruments, as compared to prior art cassettes.

Figure 1:
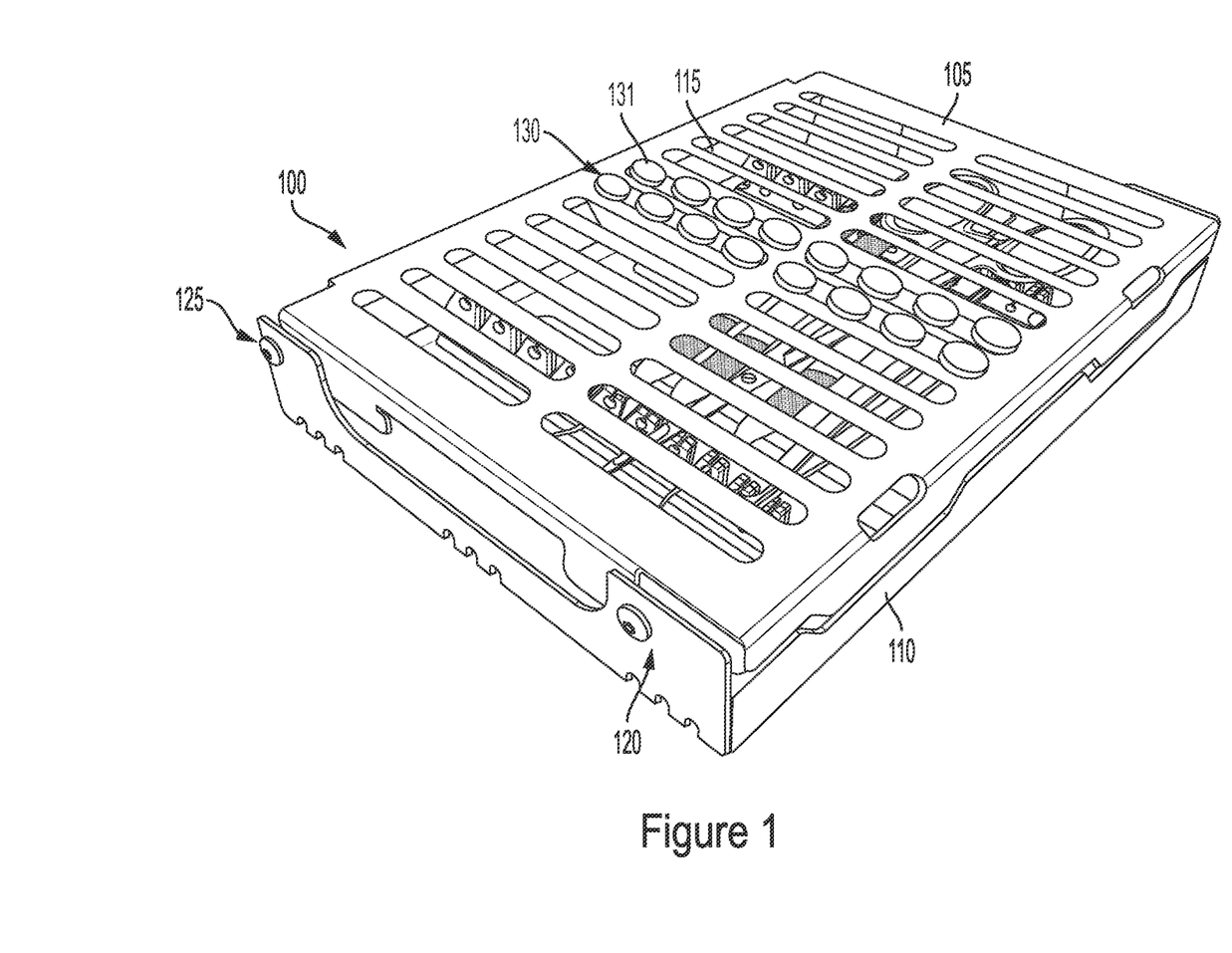
FIG. 1 is a top perspective view of a cassette in the closed position according to at least some of the presently disclosed embodiments.

As shown in FIG. 1, a cassette 100 includes a first portion 105 pivotably coupled to a second portion 110. The first 105 and second 110 portions can include apertures 115 for permitting sterilizing fluid and other liquids to enter the cassette 100 and sterilize or otherwise clean the instruments inside. The cassette 100 couples together with a coupling mechanism 120 at a first end, and pivots the first portion 105 about the second portion 110 at a second end opposite the first end. The cassette 100 can also include inserts 130 removably coupleable to the first 105 or second 110 portions for holding surgical instruments inside the cassette 100 during cleaning, as will be described below in more detail. The inserts 130 can couple to the first 105 or second 110 portion with caps 131 that extend through the apertures 115 from the inside, and extend over the apertures 115 on the outside, to maintain the position of the insert 130.

Figure 2:
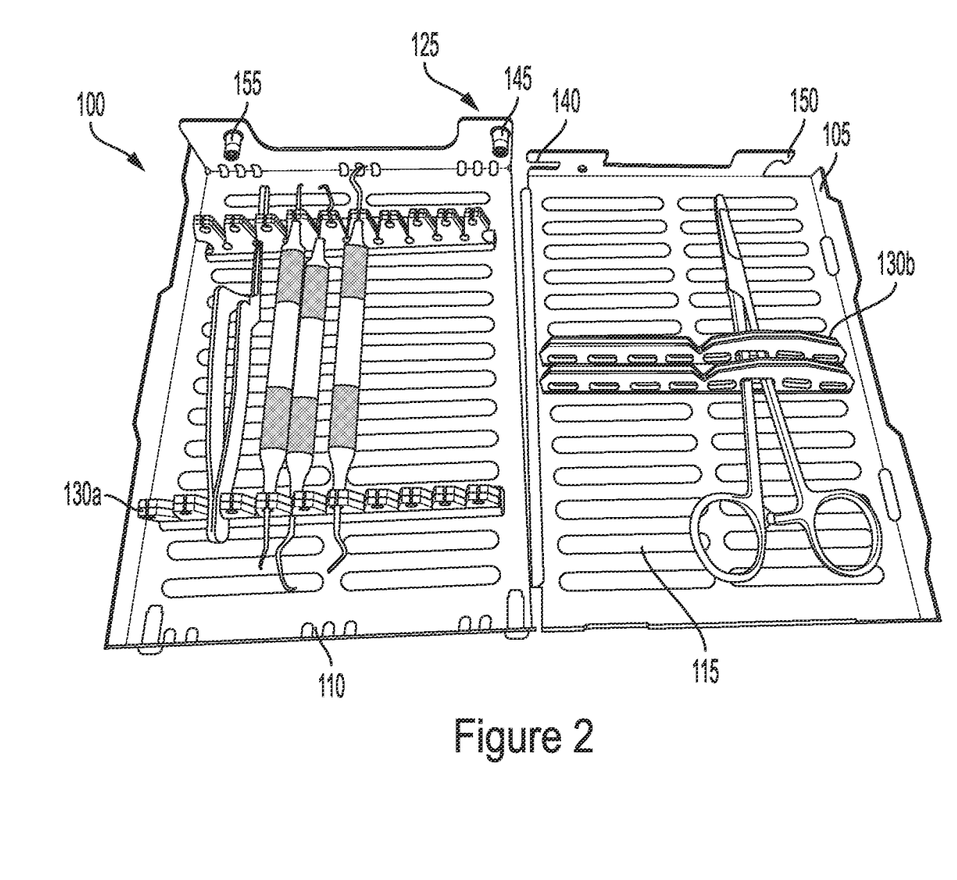
FIG. 2 is a top view of a cassette in the open position according to at least some of the presently disclosed embodiments.

FIG. 2 is a top view of a cassette in the open position according to at least some of the presently disclosed embodiments. As shown, the insert 130 can be a first insert 130a or a second insert 130b. The different inserts 130a, b can hold instruments in different manners and, accordingly, one insert can be designed to hold a particular instrument better than another insert. For example, as shown, the first insert 130a is designed to better hold a scaler, scalpel, or explorer. However, the second insert 130b includes an opening in its interior to better hold pliers or other larger instruments.

The pivot system 125 can include a slot 140 and pivot pin 145 that engage one another to pivot the first portion 105 about the second portion 110. The coupling system 120 can include a coupling pin 155 on the second portion 110 that can be engaged by a hook 150 on the first portion 105. Together, the pivot system 125 and coupling system 120 allow the first portion 105 to slide about the second portion 110 and couple or decouple the portions 105, 110 together according to user actuation.

Figure 3:
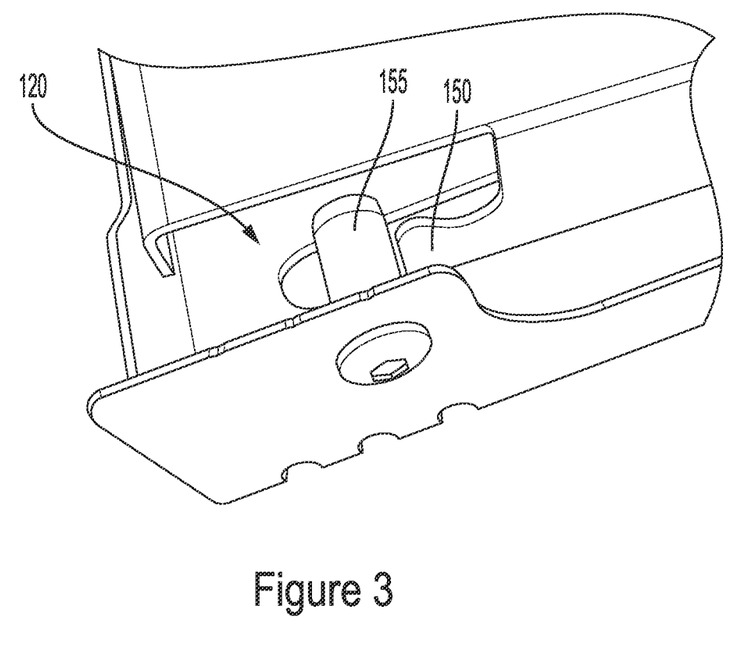
FIG. 3 is an enlarged view of the coupling mechanism according to at least some of the presently disclosed embodiments.

As shown in FIGS. 2 and 3, The cassette 100 illustrates coupling systems 120 on an upper and lower side of the first 105 and second 110 portions, allowing the portions 105, 110 to be coupled together. For example, to close the cassette 100, a user need only slide the first portion 105 laterally against the second portion 110 to allow the hook 150 of the first portion 105 to ride on and, subsequently, engage the coupling pin 155 of the second portion 110. In some instances, the two portions 105, 110 can be biased in the open position by the inserts 130. For example, the flexible second insert 130b can press against the first insert 130a, or instruments held by the first insert 130a, or the second portion 110, biasing the first portion 105 upward and away from the second portion 110 when the first 105 and second 110 portions are pressed against one another. In this manner, the hook 150 can be pressed against the coupling pin 155 in the closed position and biased against the coupling pin 155 by the flexible second insert 130b pressing against the other objects (or, more broadly, with one or more of the flexible inserts 130 pressing against another object to bias the cassette 100 in the open position). This configuration allows for better engagement of the hook 150 against the coupling pin 155 in the closed position, while allowing easier removal of the hook 150 from the coupling pin 155 when moving into the open position.

Figure 4:
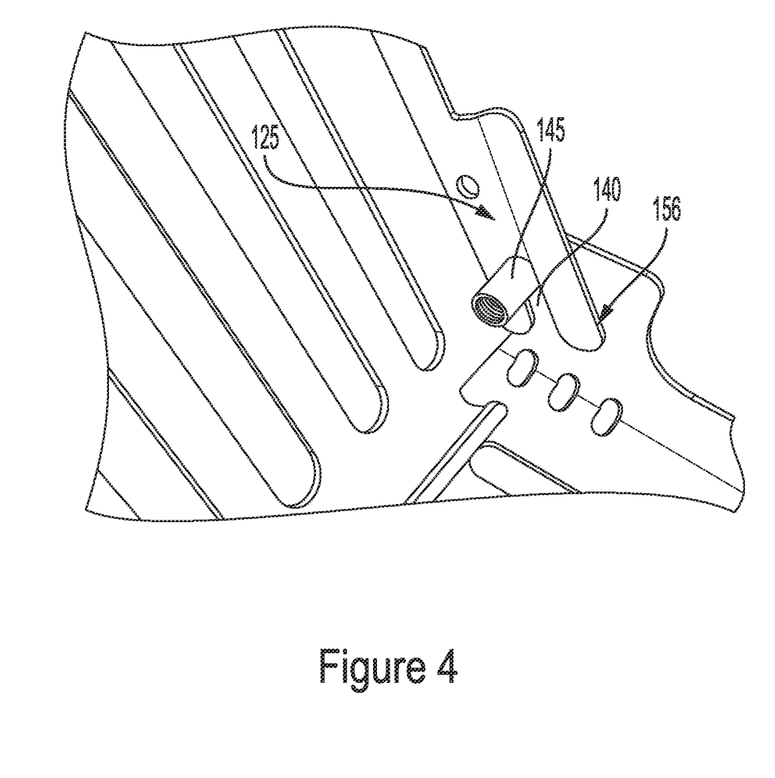
FIG. 4 is an enlarged view of the pivot system according to at least some of the presently disclosed embodiments.

As shown in FIG. 4, the pivot system 125 can include a C-shaped engagement portion 156 with a slot 140 defined therein. The engagement portion 156 can pivot about the pivot pin 145 by inserting the engagement portion 156 into the pivot pin 145 at the slot 140, as shown in FIG. 4. In this manner, the first portion 105 can pivot with respect to the second portion 110 in a secure manner as compared to the prior art. For example, the pivot pin 145 can be held secure within the slot 140 during the pivot process and not escape from the slot 140 unless the engagement portion 156 is definitively lifted away. To close the cassette 100, a user can simply pivot the first portion 105 about the second portion 110 with the pivot pin 145 fully inserted into the slot 140, and then slide the first portion 105 into the second portion 110 by pushing the hook 150 past the coupling pin 155 as described above. In this manner, a more secure and controlled pivot process can be implemented to open and close the cassette 100.

Figure 5:
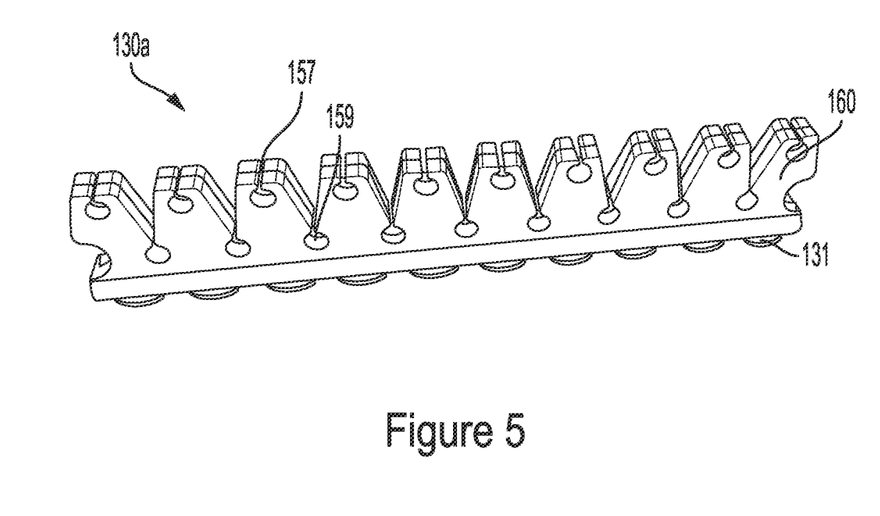
FIG. 5 is a top perspective view of a first type of insert according to at least some of the presently disclosed embodiments.

FIG. 5 is a top perspective view of the first insert 130a according to at least some of the presently disclosed embodiments. As shown, the first insert 130a can include multiple rows of indents for holding surgical instruments during the cleaning or sterilizing process. For example, the first indent 130a can include upper indents 157 spaced from lower indents 159, with both sets of indents 157, 159 being configured to hold an instrument. In this manner, the cassette 100 can be used to clean more instruments as compared to prior art cassettes 100, with the upper indents 157 and lower indents 159 forming two rows of indents as compared to the single row configuration of the prior art. The multiple rows can be spaced apart on truncated triangular bodies 160 with the upper indents 157 being located at an upper section of the bodies 160, and the lower indents 159 being located horizontally and vertically spaced from the upper intends 157, as shown.

Figure 6:
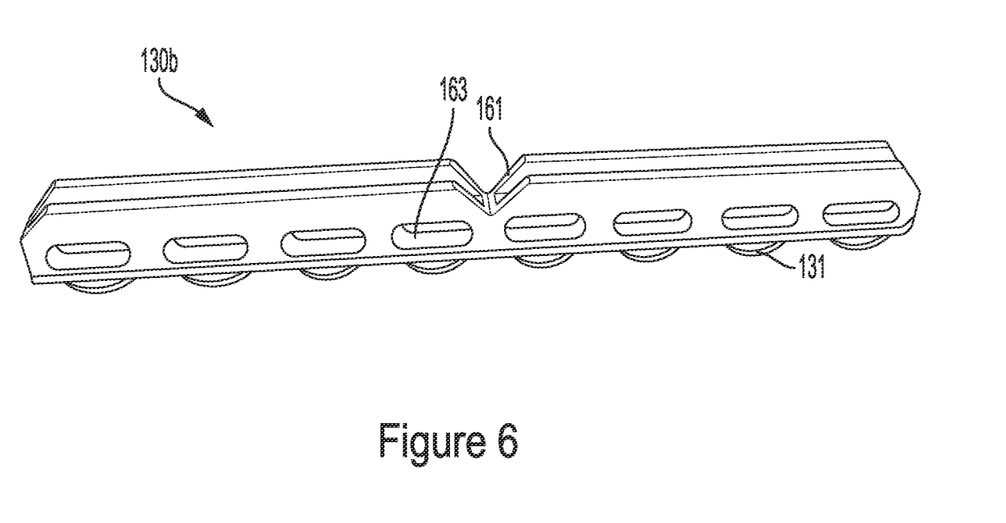
FIG. 6 is a top perspective view of another type of insert according to at least some of the presently disclosed embodiments.

FIG. 6 is a top perspective view of the second insert 130b according to at least some of the presently disclosed embodiments. As shown, the second insert 130b can include different structures that allow for larger or differently-shaped instruments to be inserted and held in place during the cleaning or sterilization process. For example, the second insert 130b can include valleys 161 for holding larger instruments that cannot be held within the indents 157, 159, and can also include an opening 163 for holding instruments such as pliers, as shown in FIG. 2. The openings 163 can be defined within the second insert 130b as surrounded holes, and the valleys 161 can be defined within the second insert 130b as sections of the second insert 130b that are open to the outside.

As discussed above, the cassette 100 can slide open or closed and can be any size cassette capable of doing so. For example, one size of the cassette can store all required surgical instruments and may therefore be better utilized by a dental or medical student who will perform a variety of different operations in a single day with less of those operations being performed on actual people where sterilization is required between operations. A practicing dentist or surgeon, however, may include several smaller cassettes where a first cassette can hold the instruments needed to perform a root canal, for example, but where a second cassette can hold the instruments needed to perform a cavity filling, for example. In this manner, the size of the cassette can be different based on the person using the cassette and the needs of that person.

The cassette 100 can be made of any material but, in a preferred embodiment, is made of stainless steel. Similarly, the inserts 130, 130a, 130b can be made of any material, but in a preferred embodiment, are made of medical-grade silicone.

The cassette 100 can hold any variety of instruments, including dental instruments, surgical instruments, medical instruments, veterinary instruments, or any other instruments where sterilization is necessary or helpful.

As used herein, the term "coupled" and its functional equivalents are not intended to necessarily be limited to direct, mechanical coupling of two or more components. Instead, the term "coupled" and its functional equivalents are intended to mean any direct or indirect mechanical, electrical, or chemical connection between two or more objects, features, work pieces, and/or environmental matter. "Coupled" is also intended to mean, in some examples, one object being integral with another object.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of the inventors' contribution. The actual scope of the protection sought is intended to be defined in the following claims when viewed in their proper perspective based on the prior art.

What is claimed is:

1. A cassette comprising:
a first portion;
a second portion separable from the first portion;
a hook coupled to one of the first or second portions;
a coupling pin coupled to the other of the first or second portions and engageable with the hook to couple together the first and second portions at a first end;
a pivot pin coupled to one of the first or second portions;
an engagement portion coupled to the other of the first or second portions, the engagement portion being C-shaped and defining a slot therein, the pivot pin configured to be inserted into the slot to pivotably couple the first portion to the second portion at a second end opposite the first end.

2. The cassette of claim 1, further comprising an insert removably coupled to the first or second portion and including indents configured to hold instruments.

3. The cassette of claim 2, wherein the insert includes a first row of indents and a second row of indents spaced from the first row of indents.

4. The cassette of claim 3, further comprising a body defining the first row of indents at an upper section of the body, and a second row of indents spaced vertically and horizontally from the upper section of the body.

5. The cassette of claim 4, wherein the body is shaped as a truncated triangle.

6. The cassette of claim 2, wherein the insert includes a valley defined therein for holding instruments.

7. The cassette of claim 2, wherein the insert includes an opening defined within an interior of the insert for holding instruments.

8. The cassette of claim 1, wherein the first portion is biased against the second portion when the first and second portion are coupled together by the hook and coupling pin.

9. The cassette of claim 2, wherein the insert is made of silicone.

10. A cassette comprising:
a first portion including apertures;
a second portion including apertures and separable from the first portion, the second portion pivotably coupled to the first portion by a pivot system on a first end, and the second portion removably coupled to the first portion by a coupling system on the second end;
the coupling system including a hook biased into engagement with a coupling pin when the cassette is in a closed position;
the pivot system including an engagement portion defining a slot that receives a pivot pin to permit pivoting of the first and second portions when the cassette is in an open position; and
an insert removably coupleable to at least one of the apertures and including indents configured to hold instruments.

11. The cassette of claim 10, wherein the engagement portion is C-shaped.

12. The cassette of claim 10, wherein the insert includes a first row of indents and a second row of indents spaced from the first row of indents.

13. The cassette of claim 12, further comprising a body defining the first row of indents at an upper section of the body, and a second row of indents spaced vertically and horizontally from the upper section of the body.

14. The cassette of claim 13, wherein the body is shaped as a truncated triangle.

15. The cassette of claim 10, wherein the insert includes a valley defined therein for holding instruments.

16. The cassette of claim 10, wherein the insert includes an opening defined within an interior of the insert for holding instruments.

17. The cassette of claim 10, wherein the insert is made of silicone.

* * * * *